United States Patent [19]

Wareing

[11] Patent Number: 4,706,830
[45] Date of Patent: Nov. 17, 1987

[54] VACUUM BOTTLE WITH PRESSURE INDICATOR

[75] Inventor: Mark V. Wareing, Embsay, England

[73] Assignee: Johnson & Johnson Products, Inc., New Brunswick, N.J.

[21] Appl. No.: 390,412

[22] Filed: Jun. 21, 1982

[30] Foreign Application Priority Data

Jun. 24, 1981 [GB] United Kingdom ............... 8119435

[51] Int. Cl.[4] .................. A61M 1/00; B65D 47/00; B65D 51/00
[52] U.S. Cl. ................. 215/365; 116/270; 206/524.8; 215/260; 215/270; 215/DIG. 3; 604/318; 604/319
[58] Field of Search ............. 150/0.5, 1, 8, 55; 206/524.8; 215/253, 260, 270, 365, DIG. 3; 116/270; 604/318, 319

[56] References Cited

U.S. PATENT DOCUMENTS

| 3,205,889 | 9/1965 | Alder et al. | 150/0.5 X |
| 3,271,810 | 9/1966 | Raffe | 215/253 X |
| 3,415,405 | 12/1968 | Rausing et al. | 215/270 X |
| 3,635,724 | 1/1972 | Schaar | 215/260 X |
| 3,939,835 | 2/1976 | Bridgman | 604/318 |
| 4,015,603 | 4/1977 | Kurtz et al. | 604/318 |
| 4,031,847 | 6/1977 | Sullivan | 116/270 X |
| 4,036,556 | 12/1977 | Thomas et al. | 116/270 X |
| 4,106,652 | 8/1978 | Leclabart | 215/253 |
| 4,217,988 | 8/1980 | Mills et al. | 215/253 X |
| 4,220,251 | 9/1980 | Hauri | 215/270 X |
| 4,240,481 | 12/1980 | Bayham | 150/8 |
| 4,294,247 | 10/1981 | Carter et al. | 150/8 X |
| 4,376,439 | 3/1983 | Lauterjung | 215/260 X |

FOREIGN PATENT DOCUMENTS

| 0061723 | 10/1982 | European Pat. Off. |
| 2639714 | 3/1978 | Fed. Rep. of Germany |
| 466509 | 1/1969 | Switzerland |
| 1580982 | 12/1980 | United Kingdom |
| 2051250 | 1/1981 | United Kingdom |

Primary Examiner—Stephen Marcus
Assistant Examiner—Sue A. Weaver

[57] ABSTRACT

A vacuum drainage bottle includes a chamber for receiving fluids from a patient and a pressure indicator (9,21) for measuring the pressure in the chamber. Prior to use, the pressure indicator is isolated from the chamber by means of a breakable seal. The seal may be in the form of a recessed membrane (43), which may be ruptured by depressing the pressure indicator, causing a ball (45) to bear against the membrane (43).

8 Claims, 7 Drawing Figures

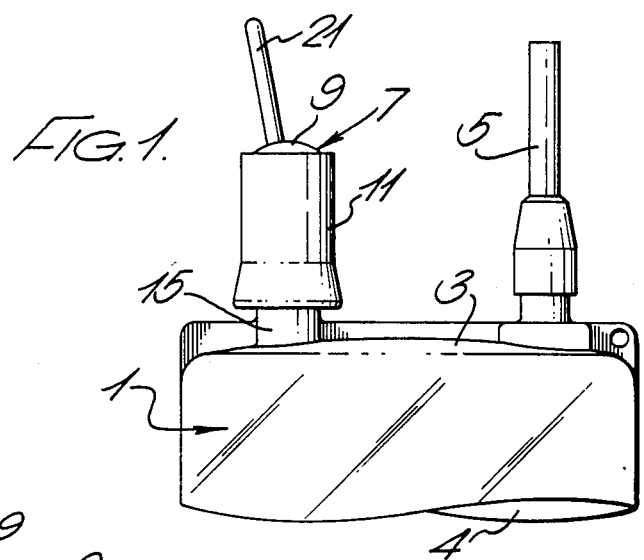
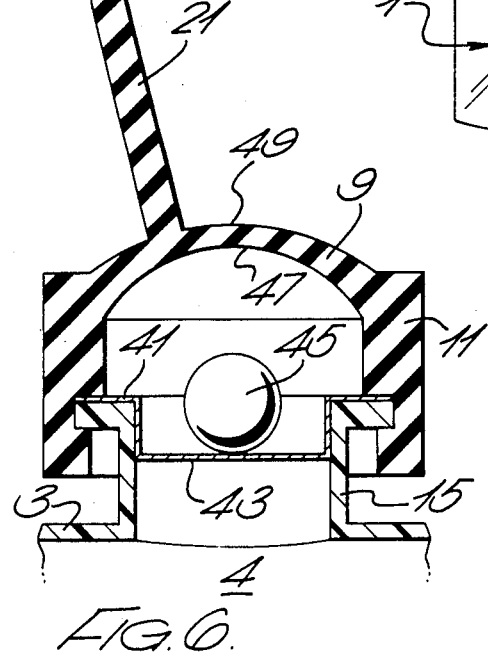
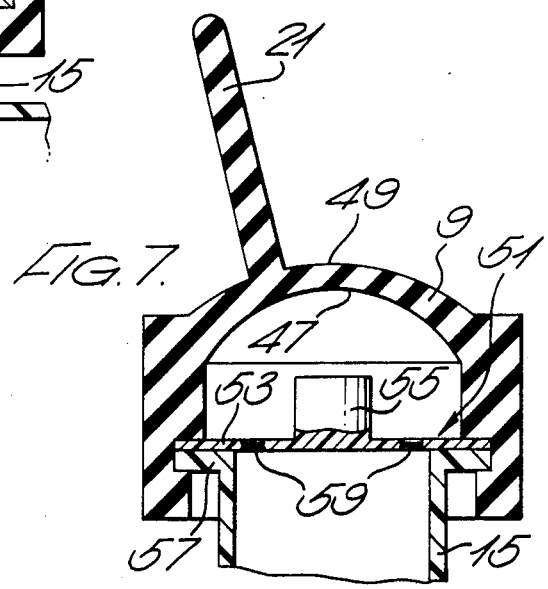

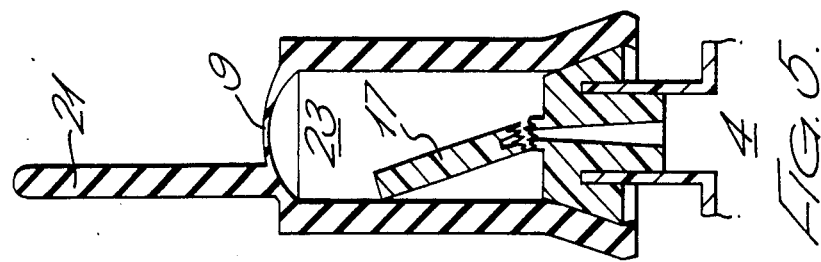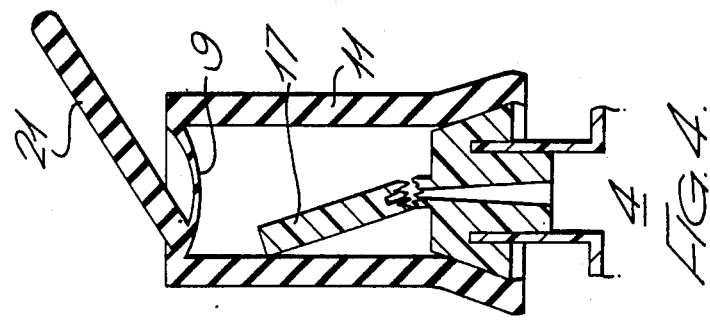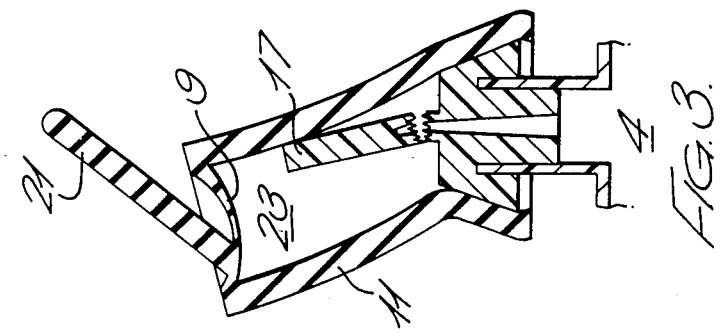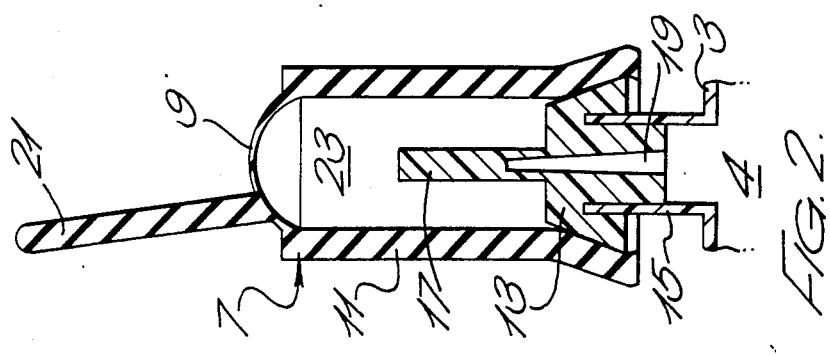

VACUUM BOTTLE WITH PRESSURE INDICATOR

This invention relates to a vacuum drainage bottle, and in particular to a vacuum drainage bottle having a pressure indicator.

Vacuum drainage bottles are commonly used in a number of medical applications for drawing various fluids from parts of a patient's body, for example from surgical wound cavities. It is usual for such vacuum drainage bottles to comprise a glass or plastics vessel provided with a stopper having two inlets. The first inlet is connected by means of a flexible tube to the area of the patient's body which is to be drained. The second inlet in connected by suitable means to an evacuation pump. When suction is applied to the second inlet, fluid is drawn from the patient into the vacuum drainage bottle via the first inlet.

An alternative form of vacuum drainage bottle is not continuously evacuated during use, but rather is pre-evacuated. This form of bottle usually comprises a glass or plastics vessel with a stopper having only one inlet. The bottle is evacuated by applying suction to the inlet, and the inlet is then closed. The bottle may be stored in the evacuated state until required, when a drainage tube is connected to the inlet, and the inlet opened. When the pressure in the bottle rises above a certain level, adequate drainage of fluids from the patient is no longer achieved. It is then necessary to replace the drainage bottle, which may either be discarded, or cleaned for re-use.

It is known to provide vacuum drainage bottles with pressure indicators. Such pressure indicators are particularly important in the case of the pre-evacuated bottle described above, in order to indicate to the nursing staff that the bottle is no longer capable of providing the necessary drainage and should be replaced. For example, British Patent Specification No. 2,041,756 describes a vacuum drainage bottle having a pressure indicator in the form of a plastics bellows.

We have found that the flexible plastics materials which have been used in the manufacture of such pressure indicators may have a significant permeability to air. Furthermore, after prolonged storage of the bottle under vacuum, a plastics pressure indicator may be deformed to the extent that the pressure indicator does not return to the null position on release of the vacuum. This may lead the nurse to believe that the bottle is still operational when, in fact, it is not.

According to the present invention there is provided a vacuum drainage bottle having a chamber for receiving fluids drained from a patient, and a pressure indicator separated from communication with said chamber by releasable sealing means.

The chamber of the vacuum drainage bottle of the present invention is not in communication with the pressure indicator until an indication of the pressure in the bottle is required. This has the advantage that leakage of air into the bottle via the pressure indicator is avoided. The bottle therefore has a longer shelf-life, and a more predictable starting vacuum. Also, plastic deformation of the indicator is avoided, because it is stressed only for a comparatively short period of time, during actual use of the bottle.

Preferably, the sealing means is irreversibly releasable, so that the pressure indicator cannot be accidentally isolated from the chamber, and thereby give an inaccurate indication of the usefulness of the drainage bottle. Preferably, the sealing means comprises an impermeable membrane, for example an aluminum foil or an aluminized plastics film, and the membrane has associated with it means for rupturing the membrane, when it is required to bring the pressure indicator into communication with the chamber of the bottle.

It is, of course, essential that the arrangement of pressure indicator, impermeable membrane and drainage chamber is such that the membrane may be ruptured without exposing the drainage chamber to the atmosphere. Conveniently, the pressure indicator (or at least a part of the pressure indicator) is sufficiently flexible that the rupturing means may be caused to bear on the membrane by depressing, or otherwise deliberately distorting, the pressure indicator.

In a particular preferred embodiment, the rupturing means is a ball, for example a metal or plastics ball, and the membranes may be recessed to receive the ball. The rupturing means may, however, be of any other convenient form, for example a pin in the shape of a conventional tack.

In an alternative embodiment, the sealing means comprises a spigot made of frangible material, the spigot having a hollow interior which is in communication with the drainage chamber but separated from communication with the pressure indicator by the material of the spigot. The arrangement is such that flexing the pressure indicator causes the spigot to fracture, bringing the pressure indicator into communication with the drainage chamber. The spigot may be made of crystal polystyrene.

Preferably, the pressure indicator includes a pressure-responsive part in the form of an elastomeric diaphragm, the configuration of which is dependent on the pressure difference across it. Preferably, the diaphragm adopts a convex configuration when unstressed, and in this state the radius of curvature of the internal surface of the diaphragm is preferably sufficiently smaller than the radius of curvature of the external surface of the diaphragm to ensure a continuous response of the diaphragm to changes in pressure across it. It is preferred to attach a pointer to the diaphragm (or to form such a pointer integrally therewith), so that the pressure indicated by the pressure indicator is more easily visible. In order to obtain maximum response of the pointer to movements of the diaphragm, the pointer is preferably positioned off-centre of the diaphragm.

A vacuum drainage bottle according to the present invention is now described, by way of example, with reference to the accompanying drawings, in which:

FIG. 1 is a side elevation of the upper portion of a vacuum drainage bottle,

FIGS. 2 to 5 are vertical sections through an arrangement of pressure indicator and vacuum seal, showing successive stages in the operation of the indicator.

FIG. 6 is a vertical section through a preferred arrangement of pressure indicator and vacuum seal, and FIG. 7 is a vertical section through a further arrangement of pressure indicator and vacuum seal.

Referring to FIG. 1, a vacuum drainage bottle comprises a generally cylindrical vessel 1, which may be of glass or plastics material. The vessel 1 is closed at its upper end by an integral cap 3 to form a chamber 4 for receiving fluids drained from a patient. The cap 3 is provided with a connector 5 and a pressure indicator 7. The chamber 4 may be evacuated by means of a vacuum line (not shown) connected to the connector 5.

The pressure indicator shown in the drawings comprises an elastomeric diaphragm 9 which is formed integrally with, and closes one end of, a hollow cylindrical support 11. In the embodiment shown in FIGS. 2 to 5, the other end of the support 11 forms a sealing fit over a spigot 13 which, in turn, forms a sealing fit inside a stub pipe 15 projecting from the cap 3. The spigot is made of frangible material, for example, plastics material, and has an elongate portion 17 which projects into the hollow of the support 11. A bore 19 extends through the spigot 13 from the chamber 4 part way into the elongate portion 17, so as to be in communication with the chamber 4, but separated from communication with the diaphragm 9 by the material of the elongate portion 17.

The diaphragm 9 has a pointer 21 formed integrally therewith. The pointer is positioned slightly off-centre of the diaphragm, and extends generally upwards, so as to be a few degrees from the vertical when the diaphragm is unstressed.

The bottle is stored in an evacuated state, with the spigot 13 separating the chamber 4 from the space 23 beneath the diaphragm 9 (FIG. 2). Since the pressure in the space 23 is substantially atmospheric, the diaphragm 9 adopts its unstressed convex configuration, as indicated by the approximately vertical position of the pointer 21. When it is desired to use the bottle to drain fluid from a patient, the nurse bends the flexible support 11, forcing it against the elongate portion 17 of the spigot 13. The elongate portion 17 is thereby fractured (FIG. 3), bringing the space 23 into communication with the chamber 4. The diaphragm 9 immediately adopts a concave configuration, as indicated by the new position of the pointer 21 (FIG. 4). The nurse then knows that the bottle is suitable for use.

As the bottle is used, the pressure in the chamber 4 gradually increases. As it does so, the diaphragm 9 (and hence the pointer 21) gradually return to their original positions. When the pointer extends vertically, but has not yet returned fully to its FIG. 2 position (i.e. slightly beyond verticality) the vacuum in the bottle has fallen to the level at which the bottle should be replaced. When the bottle is to be used in high vacuum applications, this level may be, for example, 200 mm Hg.

In the preferred embodiment illustrated in FIG. 6, the pressure indicator again comprises an elastomeric diaphragm 9 mounted on a support 11. In this case, however, the support forms a sealing fit directly with the stub pipe 15 which protrudes from the cap 3 of the bottle. At the free end of the stub pipe 15 is a vacuum seal in the form of an aluminium foil 41. The foil is provided with a recess 43 in which rests, prior to breakage of the seal, a steel ball 45.

When it is desired to use the bottle, the nurse depresses the diaphragm 9, thus forcing the ball 45 through the foil 41. The operation of the pressure indicator is then the same as that of the indicator illustrated in FIGS. 4 and 5.

The embodiment illustrated in FIG. 7 is generally similar to that illustrated in FIG. 6, except that the ball and foil arrangement of the latter is replaced by a frangible one-piece seal 51, which serves to close the upper end of the stub pipe 15. The seal 51, which may be made from a plastics material such as crystal polystyrene, is in the form of a disc-shaped membrane 53 having an integral central protrusion 55. Around the central protrusion 55, and located radially just inwardly of the lip 57 of the stub pipe 15, is an annular weakness 59 of thinner material than the remainder of the membrane 53.

When it is desired to break the seal 51, the diaphragm 9 is depressed so that pressure is brought to bear on the central protrusion 55, and the seal 51 is ruptured at the annular weakness 59.

As can be seen from FIGS. 6 and 7, the diaphragm 9 preferably has an internal surface 47 which is of smaller radius of curvature than its external surface 49. As mentioned above, this ensures that the response of the diaphragm to change of pressure is continuous. Of course, if desired, the pressure-sensitive diaphragm 9 may be so shaped as to be bi-stable i.e. so that it adopts a certain convex configuration when the pressure difference across it is less than a critical value, and a certain concave configuration when the pressure difference is above the critical value. In such a construction, it may not be necessary to have the amplifying effect of a pointer which is off-centre of the diaphragm, since the movement from the concave to the convex configuration of the diaphragm is relatively large. In this case, therefore, a pointer located in the centre of the diaphragm can be use.

What is claimed is:

1. A vacuum drainage bottle having a chamber for receiving fluids drained from a patient comprising, a connector to receive fluids from a patient, and a pressure indicator separate from said connector and separated from communication with said chamber by sealing means isolated from the atmosphere and which are releasable prior to connecting said bottle to a wound drainage tube in order to indicate the pressure in said bottle.

2. A vacuum drainage bottle according to claim 1 wherein the sealing means is irreversibly releasable.

3. A vacuum drainage bottle according to claim 2 wherein the sealing means comprises an impermeable membrane which has means associated therewith for rupturing the membrane.

4. A vacuum drainage bottle according to claim 3 wherein the rupturing means is a ball, and the membrane is recessed to receive the ball.

5. A vacuum drainage bottle according to claim 2 wherein the sealing means comprises a spigot of frangible material, the spigot having a hollow interior which is in communication with the drainage chamber, but separated from communication with the pressure indicator by the material of the spigot.

6. A vacuum drainage bottle according to claim 1 wherein the pressure indicator includes a pressure-responsive part in the form of an elastomeric diaphragm, the configuration of which depends on the pressure difference across it.

7. A vacuum drainage bottle according to claim 6 wherein the external surface of the diaphragm is convex in shape when the pressure difference across the diaphragm is zero, and under such conditions the radius of curvature of the internal surface of the diaphragm is sufficiently smaller than the radius of curvature of the said external surface to ensure a continuous response of the diaphragm to changes in pressure across it.

8. A vacuum drainage bottle according to claim 7 wherein the diaphragm carries a pointer positioned off-centre.

* * * * *